United States Patent
Khandige Sharma et al.

(10) Patent No.: US 10,465,231 B2
(45) Date of Patent: Nov. 5, 2019

(54) METHOD AND APPARATUS FOR ENRICHING PATHOGEN DNA

(71) Applicants: Divya Khandige Sharma, Bangalore (IN); Ragavendar MS, Bangalore (IN); Nivedita Mitra, Bangalore (IN); Ramya Vutukuru, Bangalore (IN); Yiwei Huang, Erlangen (DE)

(72) Inventors: Divya Khandige Sharma, Bangalore (IN); Ragavendar MS, Bangalore (IN); Nivedita Mitra, Bangalore (IN); Ramya Vutukuru, Bangalore (IN); Yiwei Huang, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 220 days.

(21) Appl. No.: 15/459,210

(22) Filed: Mar. 15, 2017

(65) Prior Publication Data

US 2017/0275670 A1   Sep. 28, 2017

(30) Foreign Application Priority Data

Mar. 22, 2016 (IN) .............................. 201631010047

(51) Int. Cl.
| | | |
|---|---|---|
| *C12Q 1/68* | (2018.01) | |
| *C12N 15/10* | (2006.01) | |
| *C12Q 1/6806* | (2018.01) | |
| *C12Q 1/6876* | (2018.01) | |

(52) U.S. Cl.
CPC ....... *C12Q 1/6806* (2013.01); *C12N 15/1013* (2013.01); *C12N 15/1017* (2013.01); *C12Q 1/6876* (2013.01)

(58) Field of Classification Search
CPC .............. C12Q 1/6806; C12N 15/1013; C12N 15/1017
See application file for complete search history.

(56) References Cited

U.S. PATENT DOCUMENTS

2012/0135454 A1* 5/2012 Walsh ...................... C12Q 1/04
435/34

FOREIGN PATENT DOCUMENTS

EP   2510123 B1   9/2014

* cited by examiner

*Primary Examiner* — David C Thomas
(74) *Attorney, Agent, or Firm* — Lempia Summerfield Katz LLC

(57) ABSTRACT

A method and an apparatus are provided for enriching pathogen DNA. The method includes adding a selective lysis buffer to a sample, incubating the mixture formed thereby, and filtering the mixture. The apparatus for enriching pathogen DNA includes: a lysis chamber; a reservoir containing selective lysis buffer, connected to the lysis chamber; and a filter connected to the lysis chamber; that achieves a limit of detection of pathogens of 500 cfu/ml or less.

13 Claims, 2 Drawing Sheets

METHOD AND APPARATUS FOR ENRICHING PATHOGEN DNA

The application claims the benefit of Indian Patent Application No. 201631010047, filed Mar. 22, 2016, incorporated by reference in its entirety.

FIELD OF TECHNOLOGY

The disclosure relates to a method and apparatus for enriching pathogen deoxyribonucleic acid (DNA) from a given sample suspected of containing pathogen cells.

BACKGROUND

Currently, the method of enriching pathogen DNA is performed by adding a selective lysis buffer to the sample and incubating the mixture formed thereby; and filtering the mixture using a filter to separate the lysed components from the pathogen cells present in the sample. The apparatuses known in the prior art for enriching pathogen DNA include a lysis chamber for accepting a sample suspected to contain pathogen cells that is connected to a reservoir containing a selective lysis buffer. The apparatus also includes a filter connected to the lysis chamber that filters the sample after lysis of eukaryotic cells.

However, such method and apparatus do not achieve limit of detection of pathogens of 500 colony forming units/milliliter (cfu/ml) or less.

SUMMARY AND DESCRIPTION

The object of the disclosure is therefore to provide a method of enriching pathogens to achieve limit of detection of pathogens of 500 cfu/ml or less.

The scope of the present disclosure is defined solely by the appended claims and is not affected to any degree by the statements within this description. The present embodiments may obviate one or more of the drawbacks or limitations in the related art.

Based on the aforementioned method, the disclosure aims to achieve the object by wetting the filter with a universal lysis buffer to lyse the filtered intact pathogen cells; passing through the filter a lysis buffer containing guanidine thiocyanate; contacting the mixture with a matrix and incubating the mixture to thereby form a complex with the pathogen DNA; and separating the complex from the mixture.

The disclosure refers to a method of enriching pathogen DNA from a given sample that is suspected to contain pathogen cells. The given sample may be a biological sample and may include, for example, whole blood. The method includes an act of adding a selective lysis buffer to the given sample to form a mixture. A selective lysis buffer is a buffer that selectively lyses cells of a particular type present in a given sample. The formed mixture is incubated to allow lysis of eukaryotic cells present in the given sample. The incubation is done at a temperature range of 20° C. to 40° C. for a time period in the range of 1 minute to 60 minutes, or 1 minute to 10 minutes. In an additional act, the mixture is filtered using a filter. The lysed eukaryotic cells are separated from the intact pathogen cells post lysis with selective lysis buffer. The intact pathogen cells remain on the filter, whereas the lysed eukaryotic cells pass through the filter and are collected as lysate.

According to an embodiment, in an additional act, the filter on which the intact pathogen cells remain is wet with a universal lysis buffer. The universal lysis buffer lyses the pathogen cells present on the filter. The universal lysis buffer may be composed of a harsh detergent, such as sodium dodecyl sulfate (SDS). The concentration of the detergent in the universal buffer is in the range of 0.1% to 0.5% volume by volume or weight by volume. Lithium acetate may also be used in the universal lysis buffer, which helps in efficient lysis of 'hard to lyse' fungi and bacterial spores. Lithium acetate also helps in recovering larger fragment nucleic acids post lysis. The concentration of lithium acetate in the universal lysis buffer is in the range of 0.01M to 0.5M. The filter is incubated at a temperature ranging from 50° C. to 90° C. for a time period in a range of 1 minute to 5 minutes. The universal lysis buffer lyses the pathogen cells present on the filter, therefore releasing the pathogen DNA.

According to another embodiment, a lysis buffer containing guanidine thiocyanate is passed through the filter in an additional act of the method. Guanidine thiocyanate is a chaotropic salt that is highly soluble in aqueous solutions. This lysis buffer is preheated and added to the filter. In an additional act of the method, the mixture is brought in contact with a matrix to form a complex with the pathogen DNA. The pathogen DNA binds to the surface of the matrix and therefore forms a complex. The binding of the pathogen DNA to the matrix is reversible and may be due to interactions such as ionic interaction or by ligands, etc. The complex is then separated out of the mixture in an additional act of the method.

According to an embodiment, the pathogen DNA bound to the matrix is quantified. Such quantification may be done, for example, by quantitative polymerase chain reaction (qPCR). Therefore, the amount of pathogen DNA isolated may be determined.

According to another embodiment, the mixture is filtered using a filter with a pore size in the range of 0.2 microns to 0.8 microns, or 0.4 to 0.6 microns. The lysed contents of the mixture pass through the filter, whereas the pathogen cells remain on the surface of the filter.

According to yet another embodiment, the mixture is filtered using a stack filter having one or more layers of filters of different pore sizes. The use of a stack filter prevents clogging of the filter with the contents of the lysate. Therefore the efficiency of filtration is higher. The stack filter may have, for example, five layers with pore sizes of 10 microns, 7 microns, 5 microns, 2 microns, and 0.45 microns, in that order.

According to yet another embodiment, the selective lysis buffer is a composition of non-ionic detergent and a buffer. The non-ionic detergent is chosen from a group including Triton X-100, Triton X-114, Tween 20, Tween 80, NP-40, Brij-35, and Brij 58. The concentration of the detergent ranges from 2% to 7%, or from 4% to 6%, and pH in the range of 8 to 10. The detergent lyses the eukaryotic cells in the given sample. The selective lysis buffer has a pH in the range of 9.5 to 11. Any buffer with a high pH may be used in the selective lysis buffer. For example, such a buffer with high pH may be sodium carbonate buffer. The concentration of the buffer is in the range of 100 mM to 300 mM.

According to yet another embodiment, the universal lysis buffer is a composition of lithium acetate and sodium dodecyl sulfate (SDS). The universal lysis buffer lyses the pathogen cells present on the filter.

According to an embodiment, the concentration of lithium acetate in the universal lysis buffer is in the range of 0.01M to 0.5M.

According to another embodiment, the concentration of SDS in the universal buffer is in the range of 0.1% to 0.5% volume by volume or weight by volume.

According to an embodiment, the lysis buffer containing guanidine thiocyanate has a pH in the range of 8 to 9.5.

According to an embodiment, the matrix is a silica coated magnetic bead. The silica coated on the magnetic bead may be in the form of, for example, silica gel. The magnetic bead includes at least one particle of ferromagnetic, ferrimagnetic, supermagnetic, or paramagnetic material. The surface of the magnetic bead is adsorptive and adheres only to DNA strands and no other components in the mixture. Silica binds to pathogen DNA in the presence of guanidine thiocyanate, therefore making the separation of pathogen DNA from the mixture easier. The concentration of guanidine thiocyanate is sufficiently high to cause the silica coated magnetic bead to bind to the pathogen DNA.

According to an embodiment, the matrix is a silica coated column. The DNA adheres to the silica on the column and therefore is separated from the mixture.

According to yet another embodiment, the complex is separated from the mixture using a magnet. The magnetic bead in the matrix is attracted to the magnet, thereby making the separation process of the complex easier.

Based on the aforementioned apparatus, the disclosure also aims to achieve the object in that the apparatus further includes a reservoir containing universal lysis buffer, connected to the filter; an incubation chamber; a reservoir containing a lysis buffer having guanidine thiocyanate, and a matrix, connected to the incubation chamber; and an analysis chamber.

The disclosure also refers to an apparatus for enriching pathogen DNA from a given sample suspected to contain pathogen cells. The apparatus includes a lysis chamber in which the eukaryotic cells present in the given sample are selectively lysed. According to an embodiment, the lysis chamber is connected to a reservoir containing selective lysis buffer. The selective lysis buffer may be made to come in contact with the sample that may be added to the lysis chamber. According to an embodiment, the apparatus also includes a filter that is connected to the lysis chamber. The filter filters the lysate from the lysis chamber and captures the pathogen cells in the pores of the filter.

According to an embodiment, the apparatus further includes a reservoir that contains a universal lysis buffer that is connected to the filter. Once the pathogen cells are captured in the pores of the filter, the universal lysis buffer is passed through the filter to lyse the pathogen cells and release the pathogen DNA.

According to another embodiment, the apparatus further includes of an incubation chamber to which is connected a reservoir containing lysis buffer having guanidine thiocyanate. The reservoir also contains a matrix. The lysate is incubated with the lysis buffer containing guanidine thiocyanate, and the matrix in the incubation chamber.

According to an embodiment, the apparatus includes an analysis chamber that may be used for further analysis of the extracted pathogen DNA.

According to an embodiment, the lysis chamber is configured to receive a sample suspected to contain pathogen cells. Such addition of sample into the lysis chamber may be done manually or may be automated.

According to another embodiment, the incubation chamber is configured to receive lysate from the filter after treatment with universal lysis buffer. The addition of lysate into the incubation chamber may be automated or may be done manually.

According to yet another embodiment, the analysis chamber is configured to receive one or more complexes from the incubation chamber. Such addition of complexes into the analysis chamber may be done manually or may be automated.

BRIEF DESCRIPTION OF THE DRAWINGS

The present disclosure is further described hereinafter with reference to illustrated embodiments shown in the accompanying drawings, in which.

DETAILED DESCRIPTION

Figure 1:
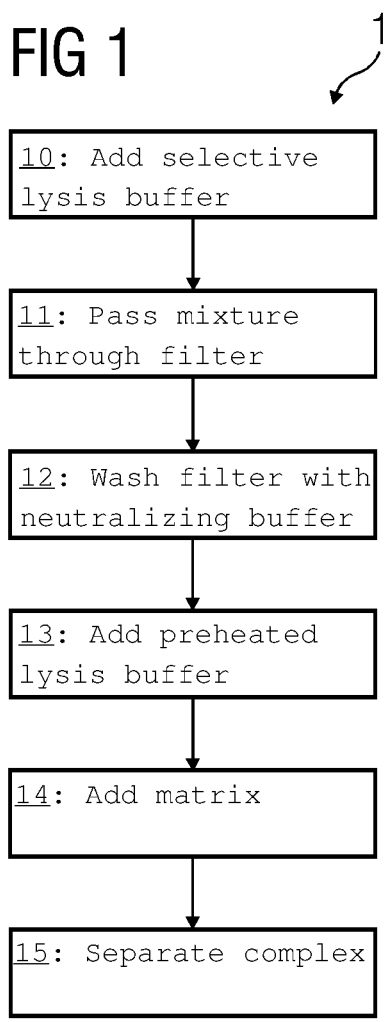
FIG. 1 illustrates a schematic diagram of a flow chart of an embodiment of a method.

Hereinafter, embodiments are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

FIG. 1 illustrates a schematic diagram of a flowchart of an embodiment of the method 1. The method 1 enriches pathogen DNA from a sample suspected to contain pathogen cells. In act 10 of the method 1, a selective lysis buffer is added to the given sample. In the embodiment described herein, the given sample is whole blood. The selective lysis buffer is a composition of a non-ionic detergent, e.g., Triton X-100 in sodium carbonate buffer. The concentration of Triton X-100 is ranging from 2% to 7%, or from 4% to 6%, in 200 mM sodium carbonate buffer. The selective lysis buffer has a pH in the range of 9.5 to 11. Around 10 ml of selective lysis buffer is added to the given sample and the mixture is vortexed and incubated at room temperature for 5 minutes. The selective lysis buffer selectively lyses the eukaryotic cells present in the given sample. Post lysis, the mixture is neutralized by addition of neutralizing buffer. In the present embodiment, the neutralizing buffer is a Tris buffer having a concentration in the range of 0.5M and 1.5M and a pH of 7.0.

In act 11, the mixture is passed through a filter. In the present embodiment, the filter used is a 25 mm GDx PVDF syringe filter having a pore size in the range of 0.2 microns to 0.8 microns, or 0.4 to 0.6 microns. Alternatively, a stack filter may also be used to filter the lysed contents of the mixture. Alternatively, the lysed mixture may also be centrifuged to isolate pathogen cells. The filter was washed with neutralizing buffer, following which the filter is wet with a universal lysis buffer in act 12. The universal lysis buffer lyses the pathogen cells concentrated on the filter to release pathogen DNA. In the present embodiment, the universal lysis buffer is a composition of lithium acetate (LiOAc) and sodium dodecyl sulfate (SDS). The concentration of lithium acetate varies from 0.01M to 0.5M or from 0.1M to 0.3M. The concentration of SDS varies from 0.1% to 5% v/v or w/v or from 0.5% to 2% v/v or w/v. The filter was incubated in the universal lysis buffer for a period varying from 10 seconds to 60 minutes or 3 to 5 minutes. The incubation was done at a temperature ranging from 50° C. to 90° C., or 70° C. to 90° C.

In act 13, a preheated lysis buffer containing guanidine thiocyanate is added to the filter. In the present embodiment, the lysis buffer used is VERSANT® lysis buffer. To the mixture formed, matrix is added in act 14. The matrix is a silica coated magnetic bead. The isolated pathogen DNA binds to the silica coated magnetic beads in the presence of guanidine thiocyanate and forms a complex. The mixture is vigorously vortexed to dislodge pathogen lysate from the beads. In act 15, the complexes are separated from the mixture using a magnet. The beads bound to pathogen DNA may be directly subjected to quantitative polymerase chain reaction (qPCR) for quantification.

Figure 2:
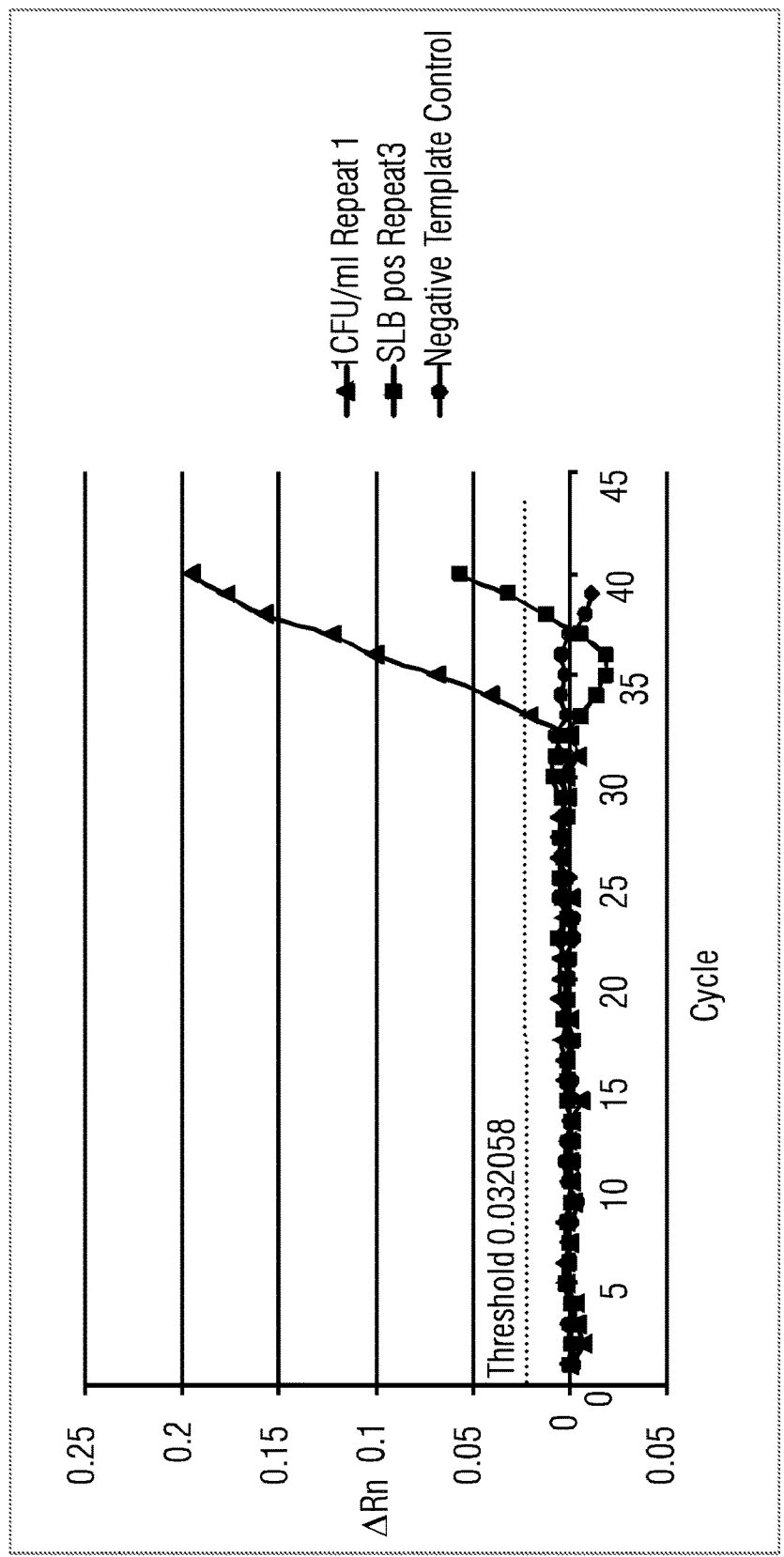
FIG. 2 illustrates a graph of the effect of selective lysis and filtration based enrichment on the detection of 1 cfu/ml *Candida tropicalis*.

FIG. 2 illustrates a graph on the effect of selective lysis and filtration based enrichment on the detection of 1 cfu/ml *Candida tropicalis*. The X-axis represents the number of amplification cycles and the Y-axis represents the intensity of normalized fluorescence. The threshold for normalized fluorescence is set at 0.032058. For the experiment, 5.0 ml fresh blood, collected in EDTA vacutainers is spiked with 5 cfu of *Candida tropicalis* to obtain blood sample with final concentration of 1 cfu/ml. Following lysis and formation of complex, the pathogen DNA was subjected to quantitative polymerase chain reaction (qPCR). The qPCR curves depicted on the graph indicate the effect of selective lysis buffer treatment and filtration on the detection of 1 cfu/ml *Candida tropicalis*. The samples that were subjected to qPCR include a positive reference that has a no blood background; a negative template control; and one repeat of the pathogen DNA obtained from the blood sample.

The $Ct_{18s\ rDNA\ average}$, an average of 3 PCR replicates for positive reference is 32.99 cycles; selective lysis buffer treated blood is 38.83 cycles; blood only treated with selective lysis buffer is undetermined; and negative template control is undetermined. Therefore, the method provides for detection of pathogen cells in the blood to a level as low as 1 cfu/ml.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

What is claimed is:

1. A method of enriching pathogen DNA comprising:
providing a sample comprising blood and pathogen cells;
adding a selective lysis buffer to the sample, wherein the selective lysis buffer selectively lyses eukaryotic cells in the sample and provides a mixture comprising the selectively lysed eukaryotic cells and intact pathogen cells;
filtering the mixture through a filter, wherein the intact pathogen cells are retained by the filter and the selectively lysed eukaryotic cells pass through the filter to provide a lysate;
wetting the filter with a universal lysis buffer to lyse the intact pathogen cells, wherein the lysed pathogen cells are released from the filter and added to the lysate;
passing an additional lysis buffer comprising guanidine thiocyanate through the filter to the lysate;
contacting the lysate with a matrix and incubating the lysate to form a complex having bound pathogen DNA; and
separating the complex from the lysate.

2. The method of claim 1, further comprising:
quantifying the bound pathogen DNA from the complex.

3. The method of claim 1, wherein the filter has a pore size in the range of 0.2 microns to 0.8 microns.

4. The method of claim 1, wherein the filter is a stack filter having one or more layers of filters of pore sizes in a range of 10 μm to 0.2 μm.

5. The method of claim 1, wherein the selective lysis buffer comprises a non-ionic detergent and a buffer, and
wherein the selective lysis buffer has a pH in a range of 9.5 to 11.

6. The method of claim 1, wherein the universal lysis buffer comprises lithium acetate and sodium dodecyl sulfate (SDS).

7. The method of claim 6, wherein a concentration of the lithium acetate in the universal lysis buffer is in a range of 0.01M to 0.5 M.

8. The method of claim 6, wherein a concentration of the SDS in the universal buffer is in a range of 0.1% to 0.5% v/v or w/v.

9. The method of claim 1, wherein the additional lysis buffer has a pH in a range of 8 to 9.5.

10. The method of claim 1, wherein the matrix comprises a silica coated magnetic bead.

11. The method of claim 1, wherein the matrix comprises a silica coated column.

12. The method of claim 1, wherein the complex is separated from the mixture lysate using a magnet.

13. An apparatus for enrichment of pathogen DNA, the apparatus comprising:
a lysis chamber configured to receive a sample comprising blood and pathogen cells;
a reservoir containing a selective lysis buffer, wherein the reservoir is connected to the lysis chamber, and wherein the reservoir is configured to provide the selective lysis buffer to the lysis chamber and selectively lyse eukaryotic cells in the sample to provide a mixture comprising selectively lysed eukaryotic cells and intact pathogen cells;
a filter connected to the lysis chamber, wherein the filter is configured to filter the mixture by retaining the intact pathogen cells and having the lysed eukaryotic cells pass through to provide a lysate;
an additional reservoir containing a universal lysis buffer, wherein the additional reservoir is connected to the filter, and wherein the additional reservoir is configured to wet the filter with the universal lysis buffer and lyse the intact pathogen cells, wherein the lysed pathogen cells are released and added to the lysate;
an incubation chamber configured to receive the lysate;
a reservoir containing an additional lysis buffer having guanidine thiocyanate, and a matrix, wherein the reservoir is connected to the incubation chamber, wherein the additional lysis buffer is configured to be passed through the filter to the incubation chamber, and wherein the lysate is configured to be contacted with the matrix in the incubation chamber to form a complex with bound pathogen DNA; and
an analysis chamber configured to receive the complex.

* * * * *

UNITED STATES PATENT AND TRADEMARK OFFICE
CERTIFICATE OF CORRECTION

PATENT NO. : 10,465,231 B2
APPLICATION NO. : 15/459210
DATED : November 5, 2019
INVENTOR(S) : Divya Khandige Sharma et al.

It is certified that error appears in the above-identified patent and that said Letters Patent is hereby corrected as shown below:

In the Claims

Column 6 (Claim 12; Line 34):
"separated from the mixture lysate using a magnet."

Should be replaced with:
"separated from the lysate using a magnet."

Signed and Sealed this
Twenty-fifth Day of February, 2020

Andrei Iancu
*Director of the United States Patent and Trademark Office*